(12) United States Patent
Liebe et al.

(10) Patent No.: US 9,907,944 B2
(45) Date of Patent: Mar. 6, 2018

(54) CONNECTING ELEMENT AND CONNECTING ASSEMBLY

(71) Applicant: W.O.M. WORLD OF MEDICINE GMBH, Berlin (DE)

(72) Inventors: Olaf Liebe, Berlin (DE); Fabian Langen, Berlin (DE); Nils Gelbert, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 162 days.

(21) Appl. No.: 14/898,072

(22) PCT Filed: Jun. 12, 2014

(86) PCT No.: PCT/EP2014/062237
§ 371 (c)(1),
(2) Date: Dec. 11, 2015

(87) PCT Pub. No.: WO2014/198828
PCT Pub. Date: Dec. 18, 2014

(65) Prior Publication Data
US 2016/0129234 A1    May 12, 2016

(30) Foreign Application Priority Data

Jun. 12, 2013 (DE) .................. 10 2013 210 922

(51) Int. Cl.
*A61M 25/16* (2006.01)
*A61M 25/18* (2006.01)
(Continued)

(52) U.S. Cl.
CPC ........ *A61M 39/1011* (2013.01); *A61M 39/00* (2013.01); *F16L 19/04* (2013.01);
(Continued)

(58) Field of Classification Search
CPC .............. A61M 39/00; A61M 39/1011; A61M 2039/0072; A61M 2039/1027; A61M 2039/1066; F16L 19/04; F16L 47/04
(Continued)

(56) References Cited

U.S. PATENT DOCUMENTS

| 5,935,112 A * | 8/1999 | Stevens | A61M 39/0613 604/167.05 |
| 2006/0217683 A1* | 9/2006 | Patania | A61M 16/08 604/533 |
| 2010/0036329 A1 | 2/2010 | Razack | |

FOREIGN PATENT DOCUMENTS

| DE | 82 14 948 U1 | 8/1982 |
| DE | 35 03 562 A1 | 8/1986 |
| WO | 2004/064895 A2 | 8/2004 |

* cited by examiner

*Primary Examiner* — Jason Flick
(74) *Attorney, Agent, or Firm* — Maschoff Brennan

(57) ABSTRACT

A connecting element for connecting two hollow bodies through which a fluid can flow comprises a first connecting part which can be brought into fluid-tight flow connection with a first hollow body through which a fluid can flow, a sealing element which is arranged at least partially in an inner area of the first connecting part and a locking element which is arranged on an outside of the first connecting part. The locking element can be transferred from an unlocked position into a locked position, wherein the locking element in the locked position acts upon the sealing element in such a way that an inside diameter of the sealing element is smaller than when the locking element is in the unlocked position.

11 Claims, 7 Drawing Sheets

(51) Int. Cl.
 *A61M 39/10* (2006.01)
 *A61M 39/00* (2006.01)
 *F16L 19/04* (2006.01)
 *F16L 47/04* (2006.01)

(52) U.S. Cl.
 CPC ...... *F16L 47/04* (2013.01); *A61M 2039/0072* (2013.01); *A61M 2039/1027* (2013.01); *A61M 2039/1066* (2013.01)

(58) Field of Classification Search
 USPC .......................................................... 604/535
 See application file for complete search history.

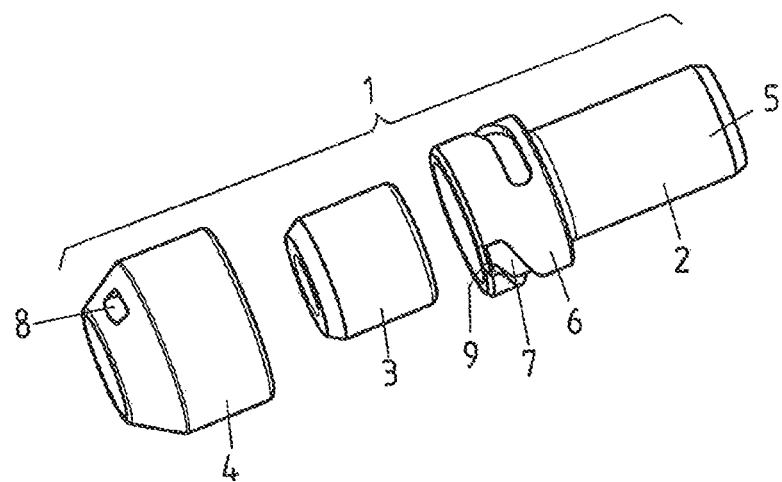
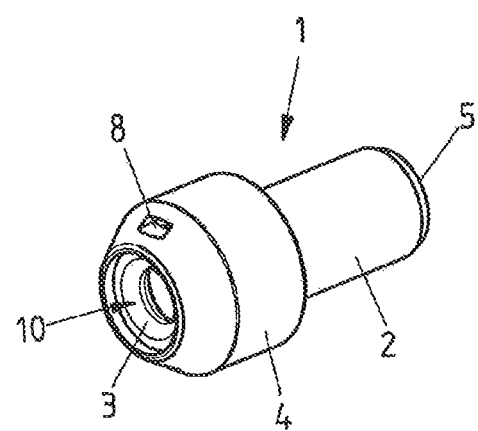

CONNECTING ELEMENT AND CONNECTING ASSEMBLY

CROSS-REFERENCE TO A RELATED APPLICATION

This application is a National Phase Patent Application of International Patent Application Number PCT/EP2014/062237, filed on Jun. 12, 2014, which claims priority of German Patent Application Number 10 2013 210 922.9, filed on Jun. 12, 2013.

BACKGROUND

The invention relates to a connecting element and to a connecting arrangement.

From prior art, numerous possible connections for connecting two tubes or other hollow bodies through which fluids can flow are known. Often, Luer Lock connectors are employed, some of which provided with a union nut for screw connecting. Such connectors seal via the contact surface between the outside of a conically formed inner cone and the outside of a likewise conically formed outer cone. A thread is here provided around the inner cone into which the outer cone can be screwed by means of a correspondingly formed protrusion. Additionally, such Luer Lock connectors can be locked by a union nut in order to prevent an unintentional opening. The inner cone is here also referred to as male Luer Lock fitting and the outer cone as female Luer Lock fitting.

What is problematic when forming such a connection by means of a Luer Lock connector is the insufficient tightness of such connections on the one hand, and, on the other hand, the small inside diameter of the male Luer Lock fitting predefined by the standard, which is 2:5 mm. Due to such a small inside diameter, the fluid flow rate through an entire system in which such a Luer Lock connector is employed is considerably limited.

In numerous instruments through which fluids flow such a limitation on the fluid flow is of no great importance, because the inside diameter of other tubes used in such instruments is even smaller. However, particularly with instruments which gases flow through higher fluid flow rates would be most desirable. For example, trocars offer a considerably larger inside diameter so that in systems in which trocars are employed the classic Luer Lock connections regularly represent a bottleneck that determines the fluid flow of the entire system.

From DE 35 03 562 A1 a crimp connector for the airtight connection of a tube, particularly of a drainage tube, is known. This drainage tube is, according to this German Patent Application, not connected with a Luer Lock fitting, but instead is housed in the crimp connector without such a fitting.

SUMMARY

An object underlying the present invention is to provide a new connecting element for tubes and other hollow bodies through which fluids can flow which guarantees a higher fluid flow than conventional Luer Lock connections and which can thereby replace such Luer Lock connections.

Preferably, a complete sealing of the connection shall be attained here and an inadvertent release of the connection shall be prevented.

This object is achieved with a connecting element having the features as described herein and with a connecting arrangement having the features as described herein.

Such a connecting element serves for connecting two hollow bodies through which a fluid can flow. It has a first connecting part, which can be brought into fluid-tight flow connection with a first hollow body through which a fluid can flow. For this purpose, the first connecting part can, for instance, be plugged into such a hollow body or placed over such a hollow body. It is furthermore possible to provide locking mechanisms such as, for instance, providing a tube clamp or adhesively bonding the connecting part and the hollow body for the fluid-tight flow connection.

The connecting element furthermore has a sealing element, which is at least partially arranged in an inner area of the first connecting part. Preferably, the sealing element is here arranged on the side of the connecting element opposite the hollow body inside of said connecting element. Finally, the connecting element also has a locking element, which is arranged on an outside of the first connecting part.

The connecting element claimed according to the invention is characterized in that the locking element can be transferred from an unlocked position into a locked position, wherein the locking element in the locked position acts upon the sealing element in such a way that an inside diameter of the sealing element is smaller than when the locking element is in the unlocked position. This reduction of the inside diameter of the sealing element caused by the action of the locking element on the sealing element here turns out such that a fluid-tight connection between the inner area of the first connecting part and an inner area of a second connecting part is provided when the second connecting part is housed in the inner area of the first connecting part. In other words, the sealing element encloses the second connecting part so tight that a fluid from the inner area of the first connecting part can get only into the inner area of the second connecting part, not, however, to an outside of the second connecting part. In case the considered fluid does not flow from the first connecting part to the second connecting part but instead in the opposite direction, the aforementioned comments on the fluid-tightness of the established connection obviously apply in an analogous manner.

The inner areas of the first connecting part and of the second connecting part are designed hollow so that a fluid can flow through them. Thus, the first connecting part represents an extension of the first hollow body, which makes a simple connection of the first hollow body to a second hollow body possible, insofar as the second hollow body is equipped with a corresponding second connecting part. The connecting element and the second connecting part, hence, represent counter pieces that can be connected to each other.

Instead of the hitherto common rigid screw connections, a flexible plug connection is realized by the novel connecting element. The connecting element serves as an expandable plug, as it were, and allows for the universal connecting of different fittings, wherein at the same time a considerably larger inside diameter is realized than is the case in solutions known from prior art. The seal between the individual components takes place here via the outer surface of a female connecting part (that is to say, the second connecting part), which is plugged into the specified connecting element. The connection is locked by the locking element, which, for instance, can be designed as a cap that is formed conically on the inside and which compresses the sealing element by means of turning, for instance.

Reducing the inside diameter of the sealing element can be realized by means of a direct contact between the locking element and the sealing element or by means of an indirect contact between the locking element and the sealing element. Thus it is conceivable, for instance, that the locking element acts upon the first connecting part, which leads to a reduction of the inside diameter of the first connecting part. Such a reduction of the inside diameter of the first connecting part would then result in a reduction of the inside diameter of the sealing element. Furthermore, it is also possible, however, that the locking element directly presses together the sealing element such that the inside diameter of the sealing element is reduced.

It is not necessary here that the inside diameter of the sealing element or the inside diameter of the connecting part has the same size over the entire length of the sealing element or of the connecting part, respectively. Rather, it is conceivable that the inside diameter of the connecting part or of the sealing element varies over the length of the respective element. The term "an inside diameter" here refers to the inside diameter on a selected point of the connecting part or of the sealing element. A reduction of the inside diameter at a selected point can leave unaffected the inside diameter at other selected points of the connecting part or of the sealing element.

In an embodiment the connecting element is provided and established to house in its inner area a female Luer Lock fitting. In this embodiment, therefore, the presently specified connecting element replaces a male Luer Lock fitting. The result here is a completely differently designed realization of a seal between the female Luer Lock fitting and the presently specified connecting element in comparison to a conventional Luer Lock connector. That is, as commented on above, the seal in a conventional Luer Lock connector takes place via the contact surfaces between the outside of the cone of the male Luer Lock fitting and the inside of the cone of the female Luer Lock fitting. In the presently specified variant of the invention, however, the seal is realized via the outside of the female Luer Lock fitting (the cone formed on the inner area of the female Luer Lock fitting is of no importance at all for the tightness in this invention variant). Thereby, the female Luer Lock fitting is converted into a male part which is inserted into the presently claimed connecting element. This role reversal of individual fittings, absolutely extraordinary for a person skilled in the art, ultimately results in a larger effective cross section available for a fluid to flow through.

Preferably, the sealing element is designed and dimensioned in such a way that it lies against the inside of the connecting part so tight that no fluid can enter between the sealing element and the inside of the connecting part. The sealing element can particularly be glued into the first connecting part. Furthermore, at least in a section of the connecting part the entire inner circumference of the connecting part is covered by the sealing element. In other words, the inner contour of a section of the connecting part preferably corresponds to the outer contour of a section of the sealing element. When the inner area of the connecting part has a cross section of a circular cylinder, the sealing element is preferably formed, at least in sections, as hollow circular cylinder.

Preferably, the locking element is designed in such a way that it covers the first connecting part at least in sections. This makes possible an easy accessibility of the locking element from outside, which, in turn, allows for an easy actuation of the locking element.

In a further variant the locking element covers an entire outside circumference of the first connecting part at least in a section of the first connecting part. For example, the locking element can be configured as a cap which is placed over the connecting part on a section of the connecting part which can particularly be a terminal section. Such a design of the locking element, covering the entire outside circumference of the connecting part, allows for an especially simple handling of the locking element, as said locking element can then easily be turned or laterally shifted by a user.

In a further embodiment of the connecting element the first connecting part and the locking element engage with each other via a thread. By means of such a thread it is possible that a movement of the locking element taking place relative to the connecting part along the thread can be realized. In this manner, it is then possible to transfer the locking element from its unlocked position into its locked position (and vice versa). The thread can, for instance, be realized in a section of the connecting part. Preferably, this section is that section which is covered by the locking element. Furthermore, in the locking element a pin, a catch or another protrusion can be provided which is guided in the thread. It is basically also conceivable to provide the thread in the locking element and to provide a guide pin, a protrusion or a catch on the connecting part for guiding in the thread.

In a variant it is conceivable that the locking element can only be transferred from its unlocked position into its locked position. In this manner, the connection to be established between the hollow bodies to be connected to each other could be established exactly once. It would then be maintained permanently. This can be advantageous in some applications. More frequently, however, a reversible or releasable connection of two hollow bodies is desired. Hence, in a further alternative embodiment of the connecting element, the locking element can also be transferred back from the locked position into the unlocked position. In this manner, therefore, an already established connection between two hollow bodies can be released again.

Preferably, it can be provided that the locking element catch-lockingly engages in its locked position, so that transferring the locking element from the locked position into its unlocked position is only possible with great effort. Such a design effectively prevents an unwanted opening of the established connection.

In a further variant the locking element in its locked position exerts a clamping force onto the sealing element and, when a second connecting part is housed in the inner area of the first connecting part, onto this second connecting part also. That is to say, the tight connection between the connecting element on the one side and the second connecting part on the other side is realized by a corresponding clamping force of the locking element.

In a further variant the locking element is at least in sections designed conical. Here, preferably, the inside of the locking element is formed conical in a section. In this manner it is possible, by a relative shift of the locking element against the connecting part, to provide a maximum possible outside diameter of varying size for elements that come into contact with the locking element. In this case, these elements can particularly be the sealing element or the connecting part. By means of a corresponding conical design of an inner area of the locking element it is therefore possible to provide a clamping force which effects a reduction of the inside diameter of the sealing element.

In a further embodiment the locking element is always connected to the connecting part when the connecting element is duly used. This connection can, for instance, take place via a thread and a protrusion guided in the thread. In order to realize this variant, the locking element and the connecting part can be produced as separate structural parts and be connected to each other prior to a release for use of the connecting element. For this purpose, the locking element can, for instance, be pushed over a protrusion of the connecting part with a corresponding locking catch so that it can thereafter be guided in a thread of the connecting part but cannot, however, be separated from the connecting part without excessive effort. This facilitates the sale and the use of a correspondingly designed connecting element.

In a further variant a section of the sealing element is arranged outside of the inner area of the first connecting part. Preferably, this section is a circumferential bulge-like protrusion which extends along the entire circumference of the sealing element. By means of such a protrusion it is possible, in an especially simple manner, to predefine a defined position in which the sealing element shall be located in the connecting part for due use of the connecting element. For by a corresponding protrusion the maximum possible depth of insertion of the sealing element into the connecting part can be defined. This is particularly the case when the protrusion extends towards the outside of the sealing element. When the protrusion extends towards the inside of the sealing element, it offers the advantage that a second connecting part plugged into the sealing element (and thereby into the inner area of the connecting part) can catch-lockingly engage behind the corresponding protrusion.

The maximum possible depth of insertion of the sealing element into the first connecting part can particularly also be defined by a corresponding design of the first connecting part. Preferably, the first connecting part is here designed in such a way that it forms a ledge for the sealing element to abut upon in the inner area of the first connecting part. The ledge here has such a depth that the inside diameter of the first connecting part is essentially not different between an area in which the sealing element is arranged and an area in which the sealing element is not arranged. Such a design allows for an especially advantageous flowing of a fluid through the first connecting part, because essentially no turbulences arise.

In a further variant the section of the sealing element that is arranged outside of the inner area of the first connecting part is directly contacted by the locking element when said locking element is in its locked position. That is to say, the locking element in its locked position presses directly against that section of the sealing element that is not entirely housed in the inner area of the first connecting part. The result of this is a reduction of the diameter of the sealing element, resulting in a tight connection with the second connecting part when such a second connecting part is plugged into the inner area of the first connecting part.

In a further variant the section of the sealing element arranged outside of the inner area of the first connecting part is provided and established to encompass a protrusion of a second connecting part by means of an undercut, when such a second connecting part is housed in the inner area of the first connecting part. This is particularly possible when the sealing element has on the inside a circumferential bulge-like protrusion which can take hold behind a corresponding protrusion of the second connecting part. With such a design a clamping force exerted onto the sealing element by the locking element in its locked position ensures not only a tight connection between the first connecting part and the second connecting part, but at the same time also a locked seat of the second connecting part in the connecting element, which cannot be released without transferring the locking element into its unlocked position.

As already mentioned, the inside diameter of the first connecting part does not necessarily have to be constant over the entire length of the first connecting part. Preferably, the smallest inside diameter of the first connecting part is about 3 mm to about 15 mm, particularly about 4 mm to about 14 mm, particularly about 5 mm to about 13 mm, particularly about 6 mm to about 12 mm, particularly about 7 mm to about 11 mm and very particularly about 8 mm to about 10 mm. In this manner it is ensured that the connecting element makes possible a higher fluid flow than conventional Luer Lock fittings, for the inside diameter of male Luer Lock fittings is merely 2.5 mm. On account of the existing standard for such Luer Lock fittings, there was hitherto no reason at all for a person skilled in the art to enlarge the inside diameter of such connections.

Preferably, the smallest inside diameter of the first connecting part is determined in that section of the first connecting part through which a fluid flows, when a corresponding connection between the connecting element and a second connecting part is established. Furthermore, an inside diameter of the first connecting part reduced by a sealing element is also viewed as smallest inside diameter of the first connecting part, because said inside diameter is likewise of crucial importance for the flow or the fluid flow properties of the first connecting part. Not taken into account when speaking of the inside diameter of the first connecting part, however, is an inside diameter of the sealing element which results in a section of the sealing element that lies outside of the first connecting part and/or outside of an area that a fluid flows through when a connection is established between the connecting element and a second connecting part.

The object underlying the invention is also achieved by a connecting arrangement with the features as described herein. Such a connecting arrangement has a connecting element according to the previous explanations. Furthermore, a second connecting part is provided which is housed in an inner area of a first connecting part of the connecting element and which can be brought into fluid-tight flow connection with a second hollow body through which a fluid can flow. Such a connecting arrangement makes possible a fluid-tight connection between a first hollow body connected to the first connecting part of the connecting element and the second hollow body connected to the second connecting part. Depending on the specific design of the locking element and of the connecting part of the connecting element, a connection which cannot be released or which can be released can here be established between the first hollow body and the second hollow body.

In an alternative embodiment the second connecting part is a female Luer Lock fitting. Thereby, in modification of conventional Luer Lock connectors, a novel connecting arrangement is provided, which allows for a significantly larger fluid flow than conventional Luer Lock connectors.

Preferred embodiments of the specified connecting element are in an analogous manner applicable to the specified connecting arrangement and vice versa.

BRIEF DESCRIPTION OF THE DRAWINGS

Further details of the invention will subsequently be explained in the context of the attached figures.

FIG. 1 shows an exploded view of an exemplary embodiment of a connecting element.

FIG. 2 shows a side view of the connecting element of FIG. 1.

DETAILED DESCRIPTION

Figure 3A:
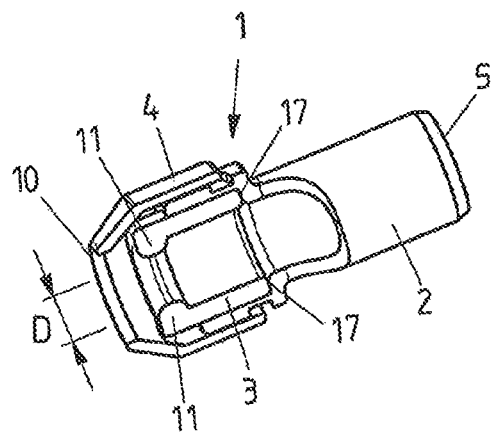
FIG. 3A shows a partially sectional view of the connecting element of FIG. 1, wherein a cap is in its unlocked position.

FIG. 1 shows an exploded view of an adapter 1 as connecting element, consisting of a first adapter part 2 as first connecting part, a seal 3 as sealing element and a cap 4 as locking element. The adapter part 2 is provided and established to be connected to a tube or any other hollow body through which a fluid or a gas can flow. For this purpose, the adapter part 2 is plugged into a corresponding tube or placed or pulled over a corresponding tube. The corresponding connection of the adapter part 2 with such a tube takes place on a first end 5 of the adapter part 2.

When the adapter 1 is duly used the seal 3 is for the most part housed in an inner area of the adapter part 2.

On a second end 6 lying opposite the first end 5, the adapter part 2 has a thread 7. This thread is provided and established so that the cap 4 can move along the thread 7. For this purpose, the cap 4 is furnished with a locking catch 8 which engages with the thread 7 and, thanks to the thread 7, can be guided when the cap 4 is turned against the adapter part 2. The adapter part 2, moreover, has a protrusion on an end 9 of the thread 7 over which the locking catch 8 has to be pressed in order to place the cap 4 on the adapter part 2. At the same time, this protrusion serves the purpose that the cap 4 cannot inadvertently be removed from the adapter part 2. Thus, in this manner it is possible to sell the adapter part 2 as a unit with the inserted seal 3 and the placed-on cap 4.

This is illustrated in FIG. 2 which represents the assembled state of the adapter 1. It can be seen in this illustration how the cap 4 covers a section of the adapter part 2, namely along the entire outside circumference of said adapter part 2. Furthermore, in this illustration in can be seen how the seal 3 is housed in an inner area of the adapter part 2, as merely an upper edge area of the seal 3 can be seen through an opening 10 formed in the cap 4. The opening 10 in the cap 4 is here dimensioned such that a further connecting part can be inserted through the opening 10 into the inner area of the adapter part 2 without problems.

FIG. 3A shows a partially sectional view through the adapter part 1 that was already illustrated in FIGS. 1 and 2. In this illustration the cap 4 is in an unlocked position in which the cap 4 sits loosely on the adapter part 2 without exerting a force on the seal 3. Thus results a first diameter D of the seal 3, which is formed between the inner sides of a circumferential bulge 11. This circumferential bulge 11 is here located on an end of the seal 3 that is facing the opening 10 of the cap 4. The circumferential bulge 11 reduces the inside diameter of the seal 3 compared to the inside diameter of the seal 3 in areas in which no circumferential bulge 11 is formed.

In an inner area of the adapter part 2 the seal 3 is coming to abut upon a ledge 17, which predefines the maximum possible depth of insertion of the seal 3 into the adapter part 2. At the same time, the ledge is here designed so deep that the size of an inside diameter in the inner area of the adapter part 2 essentially remains unchanged independently of whether one looks at a section of the adapter part 2 in which the seal 3 is arranged or at a section of the adapter part 2 in which no seal is arranged.

Figure 3B:
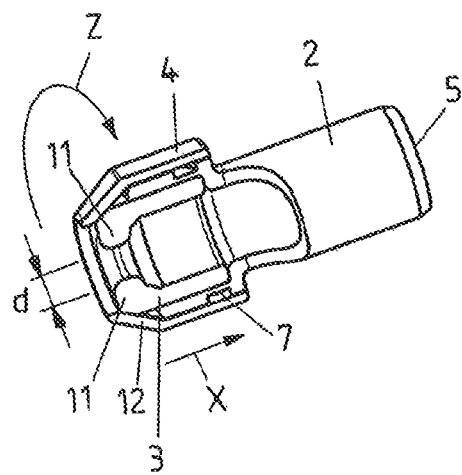
FIG. 3B shows a partially sectional view of the connecting element of FIG. 1, wherein a cap is in its locked position.

FIG. 3B now shows the adapter part 1, wherein the cap 4 has been transferred from the unlocked position into the locked position. This transfer takes place by means of a turn along a direction indicated by the arrow denoted with a Z. This turning movement leads to a lateral shift of the cap 4 in the direction of the arrow denoted with an X. That is to say, turning the cap 4 in the thread 7 of the adapter part 2 leads to a lateral shift of the cap 4 along the adapter part 2. This lateral shift causes a conically formed area 12 of the cap 4 to come into contact with the bulge 11 of the seal 3 and, due to the corresponding conical form, to press the bulge 11 together. Thereby, the diameter D formed in the area of the bulge 11 of the seal 3 in the unlocked position of the cap 4 is reduced to the inside diameter d, which is smaller than the diameter D.

Thus, the cap 4 acts on the bulge 11 of the seal 3 with a clamping force and can in this way likewise clamp objects that are housed by the bulge 11 of the seal 3. In this manner, objects in the inner area of the adapter part 2 can be locked and at the same time be sealed via the seal 3.

Figure 4:
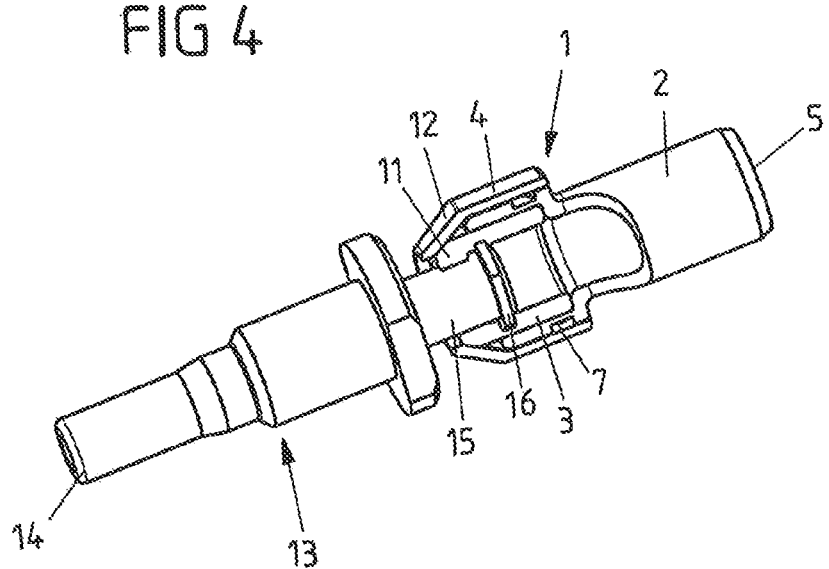
FIG. 4 shows a partially sectional view of an exemplary embodiment of a connecting arrangement.

FIG. 4 shows a partially sectional view of a connecting arrangement in which a second adapter part 13 is housed as second connecting part in the first adapter part 2. The second adapter part 13 is on its end 14 lying opposite the first adapter part 2 provided and established to be connected to a tube or any other hollow body through which a fluid or a gas can flow. When a corresponding tube is connected to the first end 14 of the second adapter part 13 and also a corresponding tube is connected to the first end 5 of the first adapter part 2, these two tubes are connected to each other via the connecting arrangement consisting of the adapter 1 and the second adapter part 13.

The adapter 1 here ensures that the second connecting part 13 is securely housed in the inner area of the first adapter part 2. For this purpose, a second end 15 of the second adapter part 13 is inserted into the inner area of the first adapter part 2. This second end 15 of the second adapter part 13 has in the exemplary embodiment of FIG. 4 a circumferential protrusion 16, which is encompassed by means of an undercut by the bulge 11 of the seal 3 when the second adapter part 13 is arranged in its due position in the inner area of the first adapter part 2. Now the cap 4 can be turned along the thread 7 in order to attain in this manner a lateral shift of the cap 4 against the first adapter part 2. Thereby, the cap 4 clamps the bulge 11 of the seal 3 with its conical area 12 against the second end 15 of the second adapter part 13 and thus locks the second adapter part 13 in a fluid-tight manner in the inner area of the first adapter part 2.

When the connection between the adapter 1 and the second adapter part 13 is to be released again, the cap 4 is moved in the opposite direction on the thread 7 so that the clamping force between the conical section 12 of the cap 4 and the bulge 11 of the seal 3 is first reduced and ultimately lifted entirely. Thereafter, the second adapter part 13 can be removed again from the inner area of the first adapter part 2.

The second adapter part 13 can particularly be a female Luer Lock fitting. According to prior art, a tube connection employing such a female Luer Lock fitting would take place in such a way that a male Luer Lock fitting would be inserted into the female Luer Lock fitting. The connection would be locked by means of a screw thread. Sealing would here take place in the inner area of the female Luer Lock fitting via the contact surface to the male Luer Lock fitting. The presently specified solution provides a completely different manner of sealing, for here, a sealing takes place on the outside of a corresponding female Luer Lock fitting by means of the bulge 11 of the seal 3. Thus, a much larger cross section is available for a fluid flowing through the second connecting part 13 and the first connecting part 2 than is the case with classic Luer Lock fittings.

Figure 5:
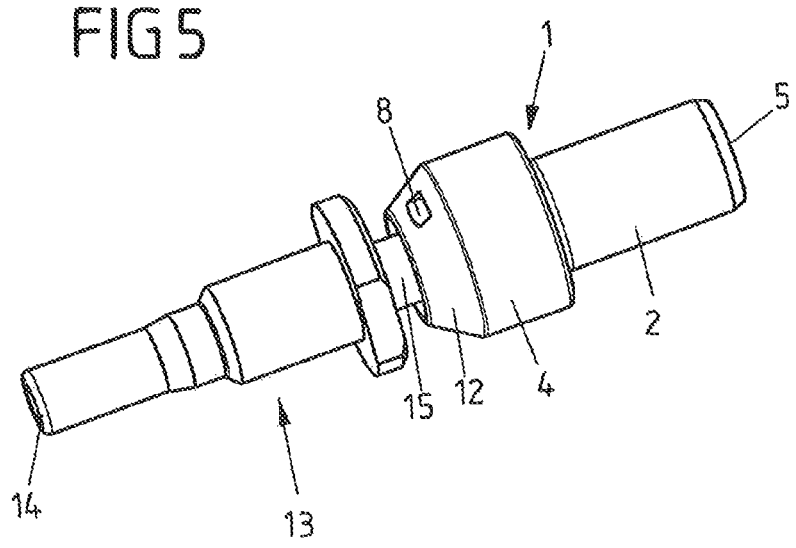
FIG. 5 shows a side view of the connecting arrangement of FIG. 4.

FIG. 5 shows the connecting arrangement of FIG. 4 in a non-sectional side view. In order to avoid unnecessary lengths, reference is made to the above explanations on the other figures for the specification of FIG. 5.

The advantageous fluid flow properties of the specified connecting element are subsequently further explained with the help of an exemplary test setup in connection with the FIGS. 6 to 9. A gas flow of varying strength was generated with an insufflator of the F114 type and channeled through a PVC tube having a length of 3 m. At the end of that tube, an exemplary embodiment of a connecting element was mounted, which was connected to a measurement device of the HRH 80 type. This measurement device can determine the fluid flow arising at the outlet of the connecting element. Moreover, this measurement device is capable of determining a pressure. For this purpose, a corresponding connection between the pressure probe of the measurement device and a T-piece arranged in front of the connecting element was established in order to, in this way, detect the dynamic pressure arising in front of the connecting element.

Figure 6:
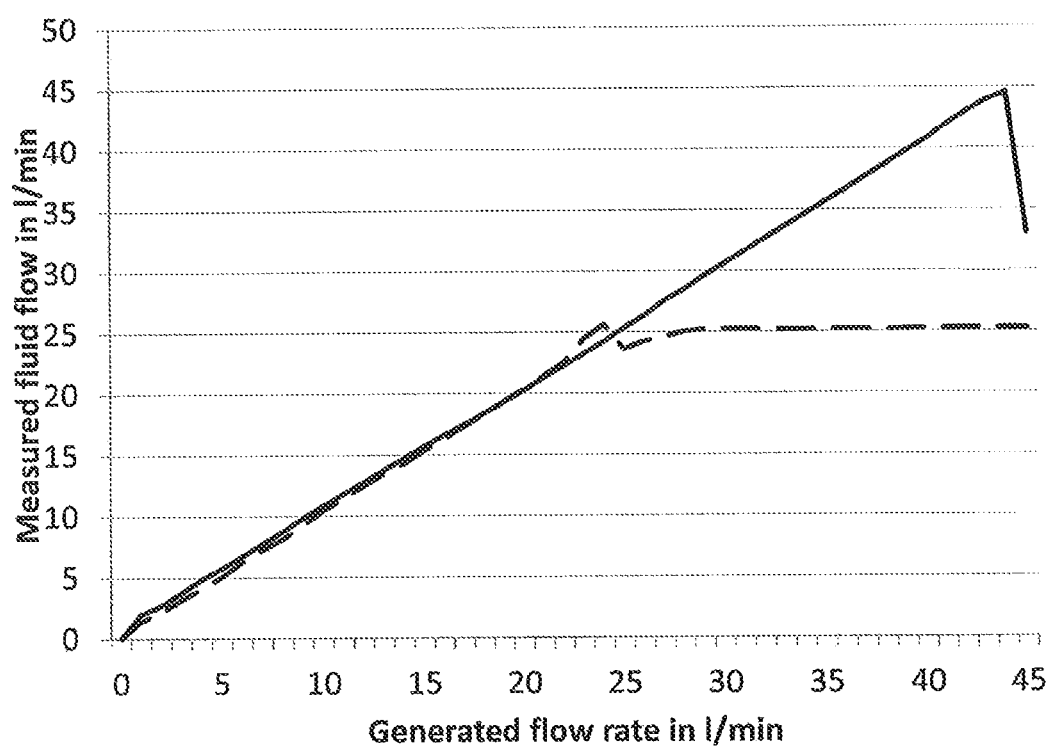
FIG. 6 shows a graphic illustration of the measured fluid flow depending on the generated flow rate in a system which is equipped with an exemplary embodiment of a connecting element.

Measurement results obtained by means of this test setup are illustrated in FIGS. 6 to 9. FIG. 6 shows a comparison of the measured fluid flow from the test system, wherein the solid curve refers to an exemplary embodiment of a connecting element according to the present invention, whereas the dashed curve relates to a male standard Luer Lock fitting known from prior art (reference measurement).

As can be seen from FIG. 6, with the novel connecting element the measured fluid flow rises continuously and proportionally to the generated flow rate up to a generated flow rate of about 43 liters per minute. Only then the functional capacity of the system is reached, which leads to a significant drop of the measured fluid flow. However, in the system known from prior art, already at about 23 liters per minute the maximum possible system capacity is reached. Even if the generated flow rate of the gas channeled through the system is then further increased, this does not result in an increase of the measured flow rate. Due to the small diameter of a male Luer Lock fitting a fluid flow of about 25 liters per minute cannot be exceeded.

Figure 7:
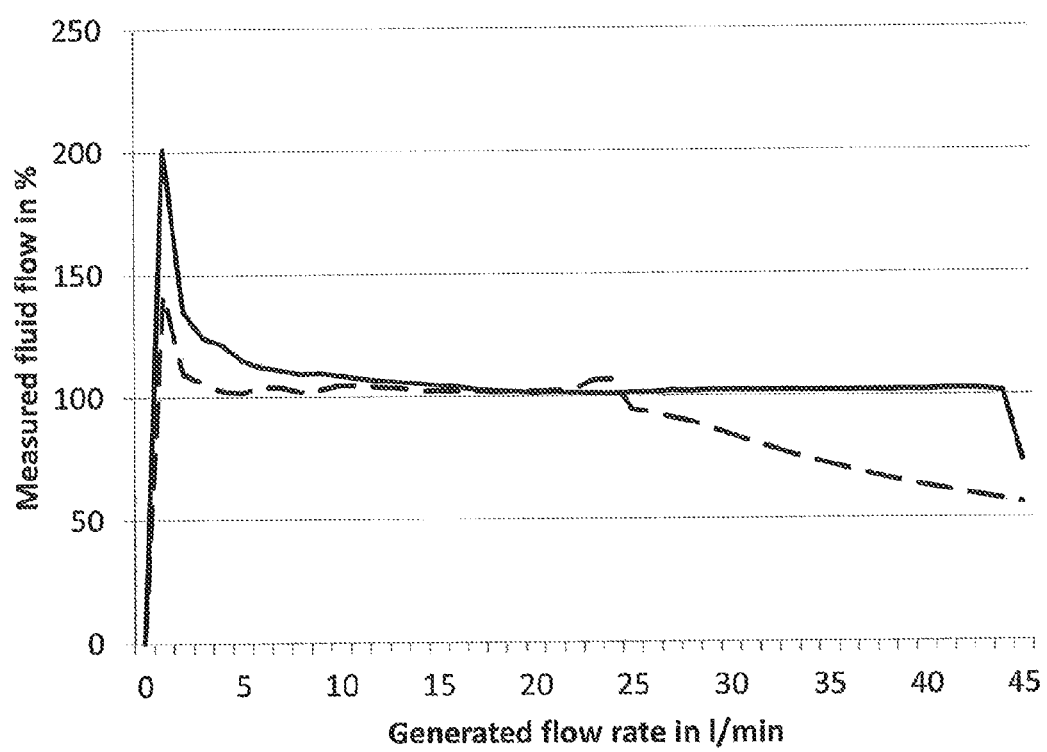
FIG. 7 shows a further graphic illustration of the measured fluid flow depending on the generated flow rate in a system which is equipped with an exemplary embodiment of a connecting element.

FIG. 7 shows the measured values of FIG. 6 in a relative illustration. Here, the measured fluid flow is plotted in percent of the generated flow rate. Yet again, the solid curve relates to the novel connecting element according to the exemplary embodiment, whereas the dashed curve relates to a male Luer Lock fitting known from prior art as reference measurement. From this illustration it is evident that up to a generated flow rate of about 43 liters per minute with the novel connecting element a fluid flow can be measured which essentially corresponds to the generated flow rate. The upward deviations at low generated flow rates are caused by measurement inaccuracies of the system. Furthermore, it can well be seen in this illustration that with the conventional Luer Lock fitting the flow falls below the 100% mark already at approximately 23 liters per minute of generated flow rate and at higher flow rates only a fluid flow lying considerably below 100% can still be measured, which is almost cut in half with just over 50% at a flow rate of approximately 45 liters per minute.

Figure 8:
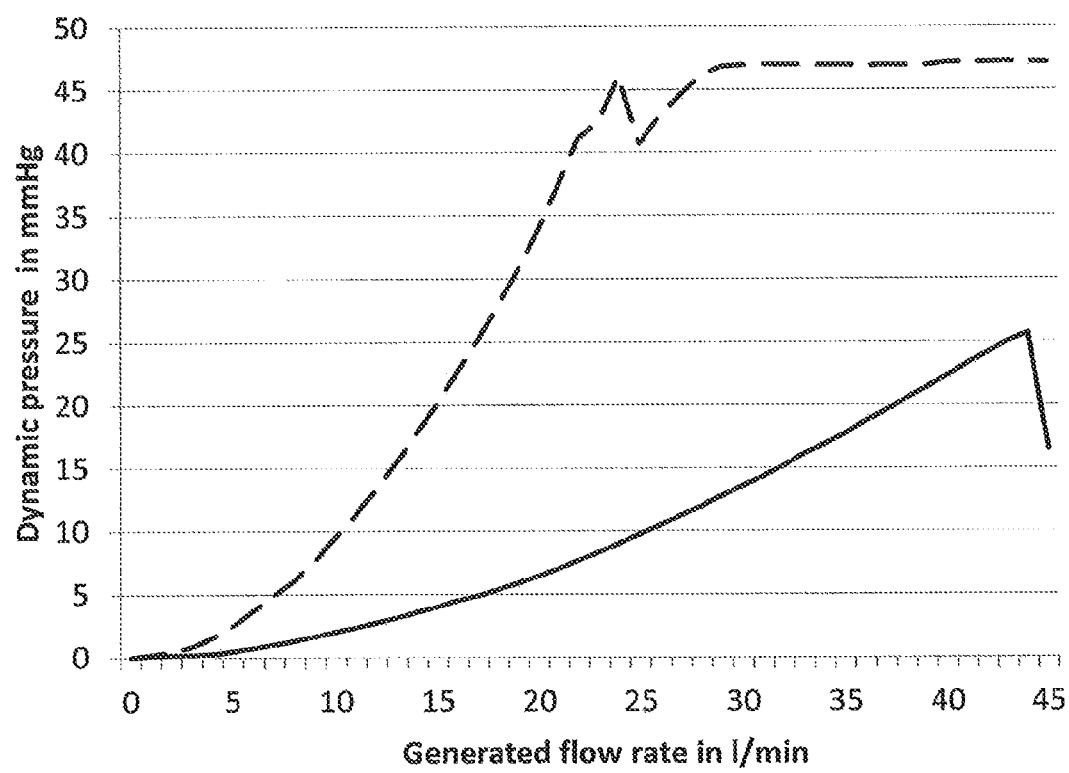
FIG. 8 shows a graphic illustration of the measured dynamic pressure depending on the generated flow rate in a system which is equipped with an exemplary embodiment of a connecting element.

In FIG. 8 the dynamic pressure measured in front of the respectively employed adapter is plotted against the generated flow rate. The solid curve again shows measured values for the exemplary embodiment of the connecting element according to the present invention, whereas the dashed curve represents measured values which were detected with a male Luer Lock fitting known from prior art. As is evident from the graphics of FIG. 8, the dynamic pressure in the system known from prior art rises significantly already at low generated flow rates. In contrast to this, with the novel connecting element there is merely a slight rise of the dynamic pressure up to a flow rate of approximately 43 liters per minute. Then the system is used to capacity, resulting in a fall in the measured dynamic pressure.

Figure 9:
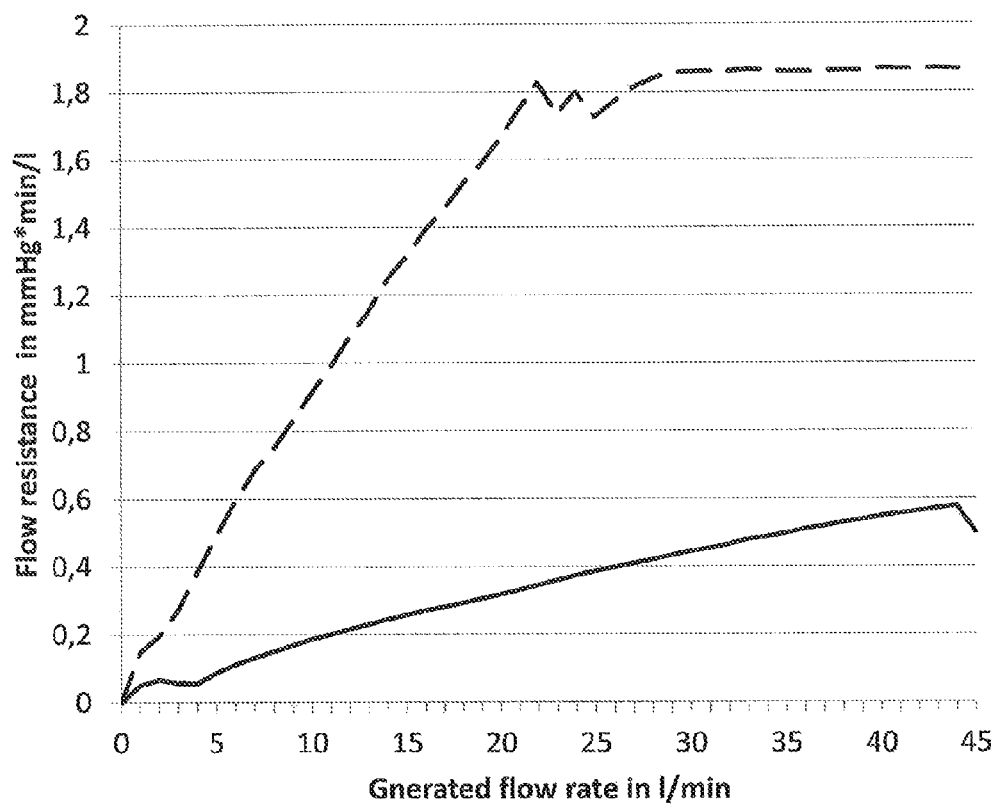
FIG. 9 shows a graphic illustration of the quotient of dynamic pressure and fluid flow depending on the generated flow rate in a system which is equipped with an exemplary embodiment of a connecting element.

FIG. 9 finally shows a graphic illustration of the flow resistance, that is, the quotient of dynamic pressure and fluid flow, against the generated flow rate. Yet again, the measured values relating to the male Luer Lock fitting known from prior art are illustrated with a dashed curve, whereas the measured values relating to the exemplary embodiment of the connecting element according to the invention are represented with a solid curve. With the novel connecting element the flow resistance rises linearly very moderately up to a generated flow rate of approximately 44 liters per minute. In contrast to this, in the system known from prior art, there is a steep rise up to a flow rate of approximately 22 liters per minute while the curve then proceeds to take a linear plateau-like course. Altogether, the flow resistance of the novel system is significantly lower than the flow resistance of the system known from prior art. Consequently, the presently specified connecting element is excellently suited for the fluid-tight connection of a tube or any other hollow body to a tube or any other hollow body while at the same time making possible a very high fluid flow while merely forming a low dynamic pressure. Furthermore, the presently specified connecting element is easy to handle and can be produced as injection molding part.

The invention claimed is:

1. A connecting element for connecting two hollow bodies through which a fluid can flow, comprising
   a first connecting part which can be brought into fluid-tight flow connection with a first hollow body through which a fluid can flow, the first connecting part having a wall surrounding and defining an hollow inner area of the first connecting part so that a fluid can flow through the inner area,
   a sealing element which is partially arranged in the inner area of the first connecting part wherein the sealing element comprises a circumferential bulge-like protrusion that is arranged outside of the inner area of the first connecting part, and a locking element which is only arranged on an outside of the first connecting part, wherein the locking element can be transferred from an unlocked position into a locked position, wherein the locking element in the locked position directly acts upon the circumferential bulge-like protrusion of the sealing element in such a way that an inside diameter of the sealing element is smaller than when the locking element is in the unlocked position, resulting in a fluid-tight connection between the inner area of the first connecting part and an inner area of a second connecting part when the second connecting part is housed in the inner area of the first connecting part, and wherein the connecting element is provided and established to house in its inner area a female Luer Lock fitting, so that in the locked position a seal over the outside of the female Luer Lock fitting is realized, when the female Luer Lock fitting is housed in the inner area of the first connecting part.

2. The connecting element according to claim 1, wherein the locking element covers the first connecting part at least in sections.

3. The connecting element according to claim 1, wherein the locking element covers an entire outside circumference of the first connecting part at least in sections.

4. The connecting element according to claim 1, wherein the first connecting part and the locking element engage with each other via a thread, wherein a movement of the locking element along the thread effects a transfer of the locking element from the unlocked position into the locked position.

5. The connecting element according to claim 1, wherein the locking element can also be transferred from the locked position into the unlocked position.

6. The connecting element according to claim 1, wherein the locking element in its locked position exerts a clamping force on the sealing element and a second connecting part housed in the inner area of the first connecting part.

7. The connecting element according to claim 1, wherein the locking element at least in sections has a conically formed design.

8. The connecting element according to claim 1, wherein the locking element, when the connecting element is in use, is always connected to the first connecting part and cannot be removed from the first connecting part inadvertently.

9. The connecting element according to claim 1, wherein the circumferential bulge-like protrusion of the sealing element is provided and established to encompass by means of an undercut a protrusion of a second connecting part housed in the sealing.

10. The connecting element according to claim 1, wherein a smallest inside diameter of the first connecting part is 3 mm to 15 mm.

11. A connecting arrangement, comprising a connecting element for connecting two hollow bodies through which a fluid can flow, the connecting element comprising a first connecting part which can be brought into fluid-tight flow connection with a first hollow body through which a fluid can flow, the first connecting part having a wall surrounding and defining an hollow inner area of the first connecting part so that a fluid can flow through the inner area, a sealing element which is at least partially arranged in an inner area of the first connecting part, and a locking element which is arranged on an outside of the first connecting part, wherein the locking element can be transferred from an unlocked position into a locked position, wherein the locking element in the locked position acts upon the sealing element in such a way that an inside diameter of the sealing element is smaller than when the locking element is in the unlocked position, resulting in a fluid-tight connection between the inner area of the first connecting part and an inner area of a second connecting part when the second connecting part is housed in the inner area of the first connecting part, and wherein the connecting arrangement further comprises a second connecting part which is housed in the inner area of the first connecting part of the connecting element and which can be brought into fluid-tight flow connection with a second hollow body through which a fluid can flow, wherein the second connecting part is a female Luer Lock fitting, wherein a seal over the outside of the female Luer Lock fitting is realized by the locking element in the locked position.

* * * * *